(12) United States Patent
Wolkenstorfer

(10) Patent No.: US 8,603,065 B2
(45) Date of Patent: Dec. 10, 2013

(54) CATHETER SYSTEM

(75) Inventor: Reinhold Wolkenstorfer, Neunkirchen (DE)

(73) Assignee: Pfrimmer Nutricia GmbH, Erlangen (DE)

( * ) Notice: Subject to any disclaimer, the term of this patent is extended or adjusted under 35 U.S.C. 154(b) by 620 days.

(21) Appl. No.: 12/445,835

(22) PCT Filed: Oct. 18, 2007

(86) PCT No.: PCT/EP2007/009064
§ 371 (c)(1),
(2), (4) Date: Apr. 16, 2009

(87) PCT Pub. No.: WO2008/046636
PCT Pub. Date: Apr. 24, 2008

(65) Prior Publication Data
US 2010/0298812 A1    Nov. 25, 2010

(30) Foreign Application Priority Data
Oct. 20, 2006  (EP) .................................... 06022077

(51) Int. Cl.
*A61M 25/00* (2006.01)
(52) U.S. Cl.
USPC ..................... 604/523; 604/103.08
(58) Field of Classification Search
USPC ................... 604/95.03, 103.08, 523
See application file for complete search history.

(56) References Cited

U.S. PATENT DOCUMENTS

| 2002/0156454 A1 | 10/2002 | Reydel |
| 2003/0018320 A1 | 1/2003 | Scheu |
| 2004/0039332 A1 | 2/2004 | Kantor |
| 2005/0215959 A1* | 9/2005 | Whitington ................... 604/278 |

FOREIGN PATENT DOCUMENTS

| DE | 29801204 U1 | 7/1998 |
| EP | 0242051 A1 | 10/1987 |
| WO | 9703810 A1 | 2/1997 |
| WO | 0053146 A1 | 9/2000 |
| WO | 2004014455 A2 | 2/2004 |
| WO | 2005097042 A1 | 10/2005 |
| WO | 2005110337 A1 | 11/2005 |

* cited by examiner

*Primary Examiner* — Kevin C Sirmons
*Assistant Examiner* — Deanna K Hall
(74) *Attorney, Agent, or Firm* — Robert R. Deleault, Esq.; Mesmer & Deleault, PLLC

(57) ABSTRACT

The invention provides a catheter system comprising a stomach probe for gastric decompression or drainage of stomach fluids, and a jejunal probe for nutriment supply during enteral feeding. The stomach probe comprises a drainage tube to be inserted into the stomach of a patient, the drainage tube having proximal and distal ends and defining a lumen for receiving and for guiding insertion of the jejunal probe into the small intestine of the patient. The jejunal probe is sized and adapted to be received within the lumen of the stomach probe for guided insertion to the small intestine. The catheter system further comprises support means for supporting the jejunal probe within the lumen of the stomach probe such that the feeding tube maintains a spaced relation to an inner wall surface of the lumen of the drainage tube.

23 Claims, 7 Drawing Sheets

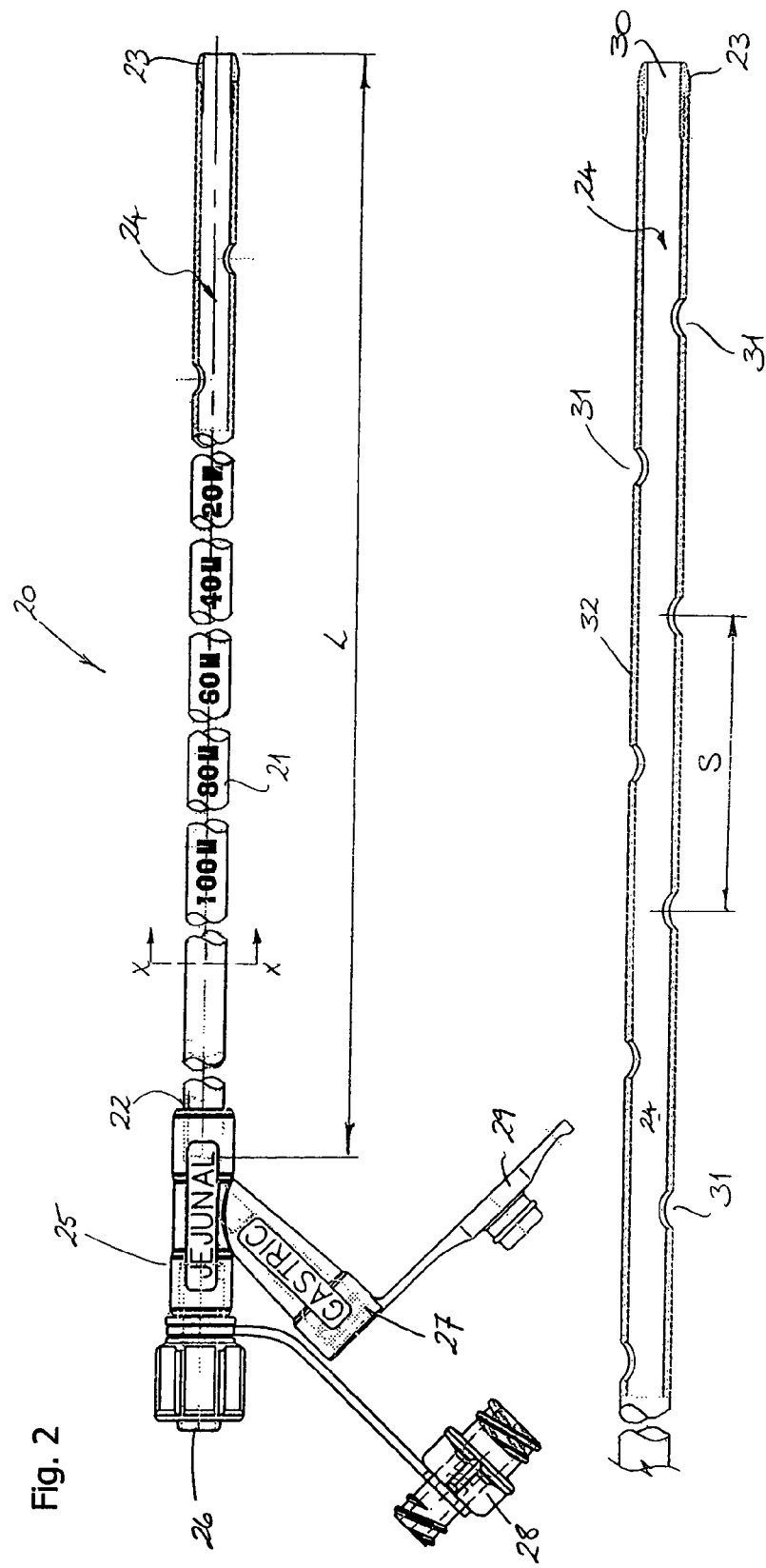

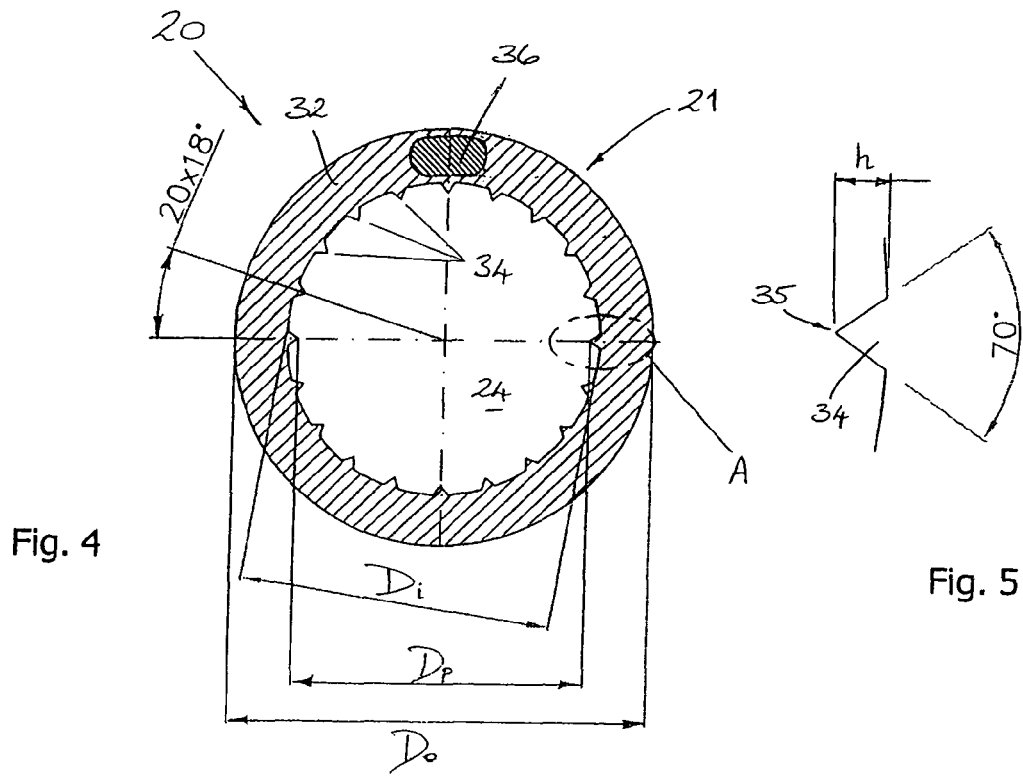
Fig. 4
Fig. 5
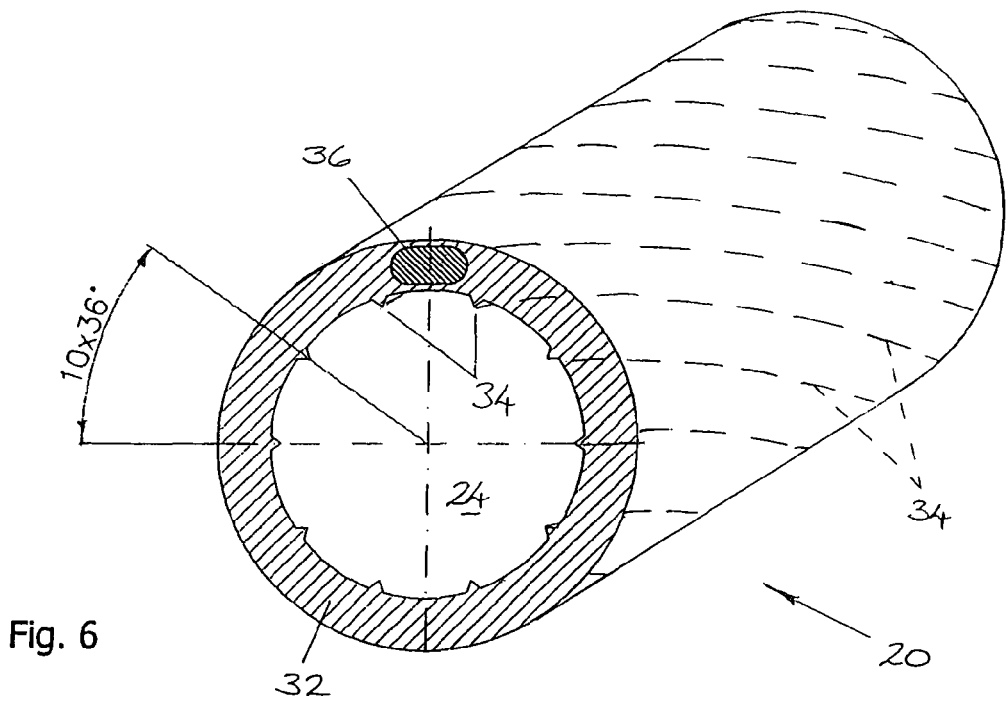
Fig. 6

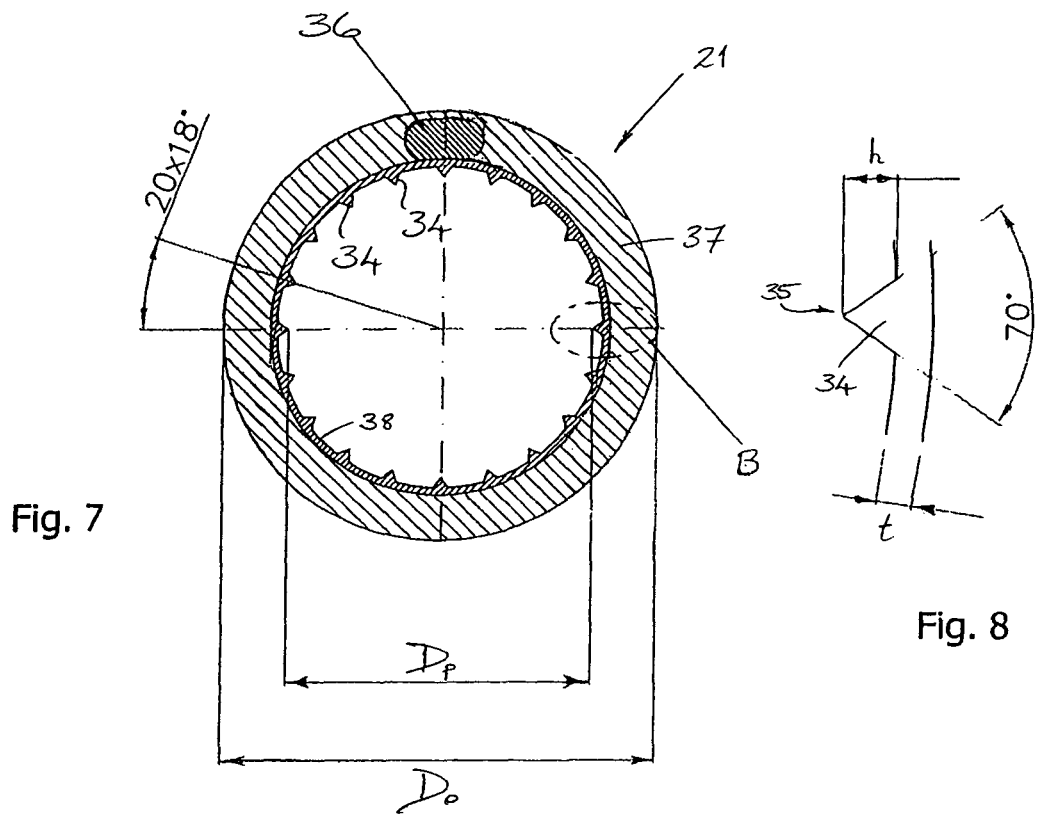
Fig. 7
Fig. 8
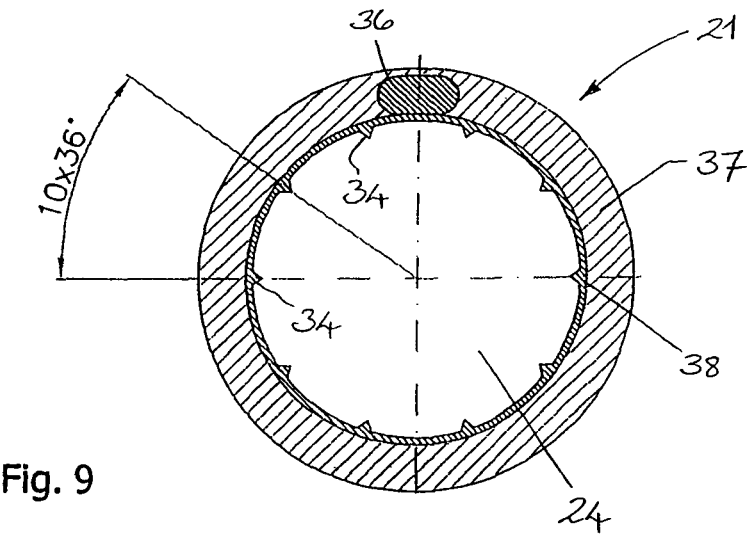
Fig. 9

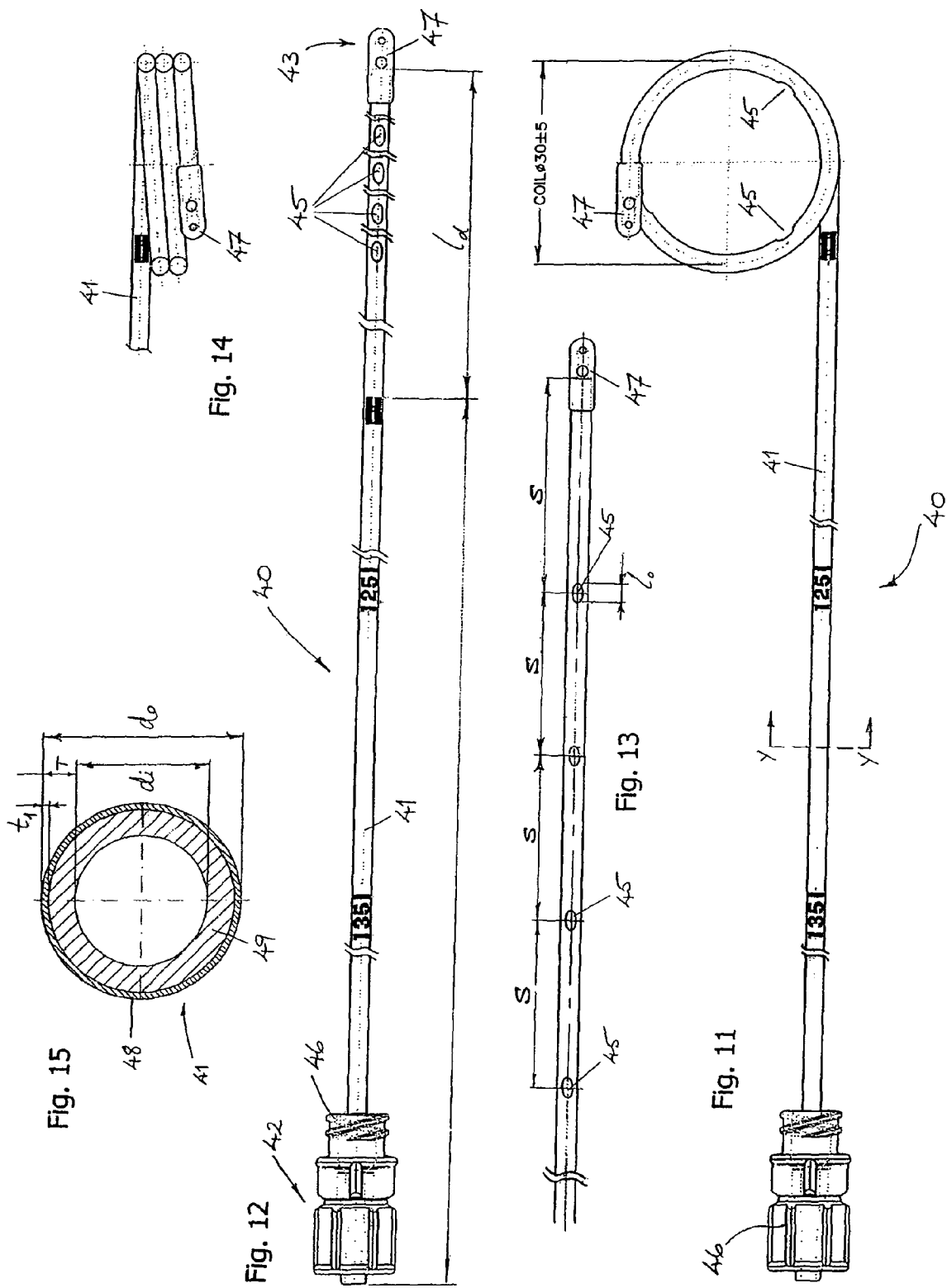

CATHETER SYSTEM

FIELD OF THE INVENTION

The present invention relates to a catheter system for deployment in the stomach and in the small intestine of a patient. In particular, the present invention relates to a catheter for providing fluid communication with the stomach of a patient for gastric decompression or drainage of stomach fluids, as well as to a catheter for providing fluid communication with the small intestine of a patient for nutriment supply during enteral feeding. The invention also relates to methods of manufacturing these catheters.

Catheters of the above-mentioned type for deployment in the stomach or in the small intestine of a patient are also referred to as "probes", and this term will also be used throughout the following description. In this regard, a catheter that is designed for deployment in the stomach for gastric decompression or drainage will also be herein referred to as a stomach probe or a gastric probe. Similarly, a catheter that is designed for deployment in the small intestine, e.g. for the supply of nutriment during enteral feeding, will be referred to as a jejunal probe (named after the jejunum—the upper part of the small intestine into which the probe is inserted) or a feeding probe. Importantly, the present invention not only relates to stomach probes and jejunal probes individually, but also to a catheter system comprising a stomach probe in combination with a jejunal probe.

BACKGROUND OF THE INVENTION

Catheters that provide fluid communication with the small intestine of a patient are typically employed for supplying nutriment to a patient during a period of post-operative recuperation. The catheter may be inserted into the small intestine via a percutaneous route, i.e. through the abdominal wall, or may alternatively be inserted nasally. Once the enteral feeding catheter is properly deployed, it may remain in position for supplying nutriment to the patient for as long as six or seven weeks. Thus, enteral feeding via a catheter in this manner is not only considerably easier to administer than intravenous nutriment supply, but is also significantly less expensive.

Naso-intestinal catheters for conveying nutriment to the small intestine are typically inserted into the jejunum via a previously deployed stomach probe. The stomach probe is designed to extend into the stomach of the patient and defines a lumen through which insertion of the jejunal probe is guided. Thus, the stomach probe has a larger diameter than the jejunal probe and, even with the jejunal probe extending through it, the lumen of the stomach probe is typically formed large enough to define a space around the feeding probe for evacuating or draining gastric fluids from the stomach during nutriment supply to the patient via the feeding probe.

Stomach probes typically have a length in the range of about 1000 mm to 1200 mm, whereas feeding probes are typically somewhat longer (e.g. 1600 mm to 2000 mm) such that they emerge from and extend beyond the stomach probe into the small intestine. When inserted through the lumen of the stomach probe, an outer surface of the feeding probe will typically be in contact with an inner surface of the lumen of the stomach probe over much of their common length. This has a number of disadvantages, including frictional resistance which may hinder deployment of the feeding probe.

In this regard, it is to be appreciated that deployment of a feeding probe through a stomach probe involves sliding a soft, flexible, small-diameter catheter along a convoluted path through the cavities of the nose, throat and oesophagus. Given the soft and flexible nature of the feeding probe, as well as a small outer diameter of only a few millimeters, it will be understood that frictional resistance between the outer surface of the feeding probe and an inner surface of the lumen in the stomach probe may complicate the insertion process. To assist in this regard, a guidewire is often employed. Furthermore, as the stomach probe is typically provided with lateral openings at its distal end region for effecting decompression and/or drainage of the stomach during the enteral feeding procedure, contact between the feeding probe and the inner surface of the stomach probe lumen may also partially block the lateral drainage holes, thereby causing a sub-optimal performance of the stomach probe.

During deployment of an enteral feeding probe, the progress of the probe into the small intestine is often monitored using an endoscope. The endoscope illuminates the site within the patient and generates video images of the probe as it is advanced towards its desired position. The progress of the probe may then be observed on a video monitor by the medical professional inserting the probe. A problem with this technique, however, is that known jejunal probes are difficult to observe under the illumination provided by many endoscopes.

Furthermore, as the small intestine is a dynamic environment subject to peristaltic movements as well as to influences of the patient moving his/her body, it is important to ensure that, once deployed, the jejunal probe remains in the desired position.

In view of the above considerations, the present invention is concerned with providing a catheter and a catheter system for deployment in the stomach and/or in the small intestine of a patient which provides for an improved inter-operability between a stomach probe and a feeding probe. The invention is also concerned with providing improved visibility of jejunal probes during observation with an endoscope. In addition, the invention aims to provide a catheter having a greater capability of maintaining its position once deployed in the small intestine.

SUMMARY OF THE INVENTION

According to one aspect, the invention provides a catheter system comprising:

a stomach probe for gastric decompression or drainage of stomach fluids, comprising a drainage tube to be inserted into the stomach of a patient, the drainage tube having proximal and distal ends and defining a lumen for receiving and for guiding insertion of a jejunal probe into the small intestine of the patient; and a jejunal probe for nutriment supply during enteral feeding, comprising a feeding tube to be inserted into the small intestine of a patient, the feeding tube defining a lumen for conveying liquid nutriment from an inlet at a proximal end thereof to one or more outlet openings formed at a distal end region of the feeding tube, the jejunal probe being sized and adapted to be received in the lumen of the stomach probe for guided insertion to the small intestine;

wherein the catheter system comprises support means for supporting the jejunal probe within the lumen of the stomach probe such that the feeding tube is in spaced relation to an inner wall surface of the lumen of the drainage tube.

Thus, the support means is adapted to maintain a clearance or spacing between the feeding tube and an inner wall surface of the lumen of the drainage tube, preferably over a substantial length of the lumen of the stomach probe, and more preferably over its entire length. Advantageously, therefore, the support means is adapted to support the jejunal probe in such a manner that fluid communication between the proximal and distal ends of the drainage tube is maintained around a circumferential extent of the feeding tube, preferably over the entire length of the stomach probe lumen. The support means may be arranged longitudinally of the catheter system between an inner wall of the lumen of the drainage tube and an outer wall of the feeding tube received therein. Furthermore, the support means is preferably adapted to allow relative movement between the feeding tube and the drainage tube, thereby facilitating insertion and withdrawal of the jejunal probe. In this regard, the support means is preferably adapted to provide low or reduced friction between the feeding tube and the drainage tube.

In a preferred form of the invention, the support means is provided on the stomach probe and comprises at least one projection which projects inwardly from a wall of the drainage tube into the lumen of the stomach probe such that the projection is adapted to form a support for contact with an outer surface of the jejunal probe when it is received within the lumen.

In an alternative form of the invention, however, the support means may be provided on the jejunal probe. In this form, the support means comprises at least one projection which projects outwardly from a wall of the feeding tube such that the projection is adapted to form a support for contact with an inner wall of the lumen of the stomach probe when it is received therein.

In each case, in order to minimise friction generated as the jejunal probe is inserted through the lumen of the stomach probe, the support surface of the at least one projection is preferably formed to be relatively small. Accordingly, the at least one projection preferably has a cross-section that becomes progressively smaller from a base region adjacent the wall of the tube towards the support surface of the projection. For example, the cross-section of the projection may taper uniformly from the base region to the support surface and it may present a rounded support surface. Alternatively, the cross-section of the at least one projection may have an entirely rounded form, e.g. semi-circular, thereby presenting a curved support surface for line contact with the jejunal probe or the stomach probe, as the case may be.

In a preferred form of the invention, the catheter system comprises a plurality of these projections, each forming a support for maintaining the feeding tube in spaced relation to the drainage tube when the jejunal probe is received within the stomach probe. The projections are preferably arranged or distributed substantially evenly in both of the longitudinal and circumferential directions on the drainage tube or the feeding tube, respectively. The projections are thus adapted to ensure or define a minimum spacing or clearance between the feeding tube and the drainage tube, but the projections are typically dimensioned to provide a gap or a certain amount of 'play' between the two tubes in the radial direction, e.g. when the feeding tube is centrally positioned within the drainage tube. Accordingly, in use, the actual spacing or clearance between the two tubes at any given point along the length of the drainage tube lumen may vary. When provided on the outer surface of the feeding tube, the projections are preferably only provided over the longitudinal extent of the feeding tube that is received within the lumen of the stomach probe. When provided on the stomach probe, on the other hand, the projections are typically only provided within the lumen of the drainage tube.

According to another aspect, therefore, the present invention provides a catheter to provide fluid communication with the stomach of a patient for gastric decompression or drainage of stomach fluids, the catheter comprising a tube to be inserted into the stomach of a patient, the tube having proximal and distal ends and defining a lumen for receiving and for guiding insertion of a probe into the small intestine of the patient. The tube includes support means projecting from a wall of the tube into the lumen to form a support for contact with an outer surface of the probe when it is received within the lumen. Thus, the support means comprises at least one projection which projects inwardly from a wall of the tube into the lumen. In this regard, the projection presents a support surface for contact with the outer surface of the probe, with the support surface preferably located at a radially innermost region of the projection. The projection is thereby adapted to form a support for contact with an outer surface of the probe when it is received within the lumen.

In order to minimise friction generated as the probe is inserted through the lumen, the support surface of the projection is preferably formed to be relatively small. The projection preferably has a cross-section that becomes progressively smaller from a base region adjacent the wall of the tube towards the support surface. For example, the cross-section of the projection may taper uniformly from the base region to the support surface. Alternatively, it may have a curved (e.g. hemispherical) form.

In a preferred form of the invention, the projection is elongate and extends along the wall of the tube in the form of a rib. The rib may extend in a longitudinal direction of the tube, or in a circumferential direction of the tube, or in both of the longitudinal and circumferential directions, e.g. helically. The support surface of the rib-like projection may therefore be a rounded tip or ridge which effectively makes only line contact with the outer surface of the probe.

In a preferred form of the invention, the support means comprises a plurality of projection from the wall of the tube, with each of the projections forming a support for contact with the outer surface of the probe received within the lumen. The projections are preferably arranged substantially evenly over the wall of the tube in both of the longitudinal and circumferential directions.

According to another aspect, the invention provides a method of manufacturing the catheter described above, comprising the steps of:
provisioning an extrusion die for forming a tube, the extrusion die defining a cavity for forming a wall of the tube and at least one recess in communication with the wall-forming cavity, the at least one recess extending radially inward from the wall-forming cavity; and
extruding a polymer plastic material through the extrusion die to form a tube defining a lumen, whereby extrusion of the polymer plastic material through each recess forms an elongate rib which projects radially inwardly from the wall of the tube into the lumen and extends longitudinally along the length of the extruded tube.

In a preferred form of the invention, the method further comprises the step of rotating the extrusion die during the extrusion step such that each rib has a twisted or helical form over the longitudinal extent of the tube. The extrusion die may be provided in an extrusion nozzle, such that the step of rotating the extrusion die comprises rotating the extrusion nozzle.

According to a further aspect, the invention provides a catheter system comprising:
a stomach probe consisting of a catheter as described above; and a jejunal probe for nutriment supply during enteral feeding, comprising a feeding tube to be inserted into the small intestine of a patient, the feeding tube defining a lumen for conveying liquid nutriment from an inlet at a proximal end thereof to one or more outlet openings formed at a distal end region of the feeding tube, the jejunal probe being sized and adapted to be received in the lumen of the catheter for guided insertion to the small intestine.

According to an alternative aspect, the invention provides a catheter for providing fluid communication with the small intestine of a patient for nutriment supply during enteral feeding. The catheter comprises a tube for insertion into the small intestine of a patient through a stomach probe, the tube defining a lumen for conveying liquid nutriment from an inlet at a proximal end of the tube to one or more outlet openings formed at a distal end region of the tube. In this aspect of the invention, the feeding tube includes support means projecting outwardly from a wall of the tube to form a support for contact with an inner surface of a lumen in the stomach probe when the catheter is received within the stomach probe.

Thus, according to this alternative aspect of the invention, the support means comprises at least one projection which projects outwardly from the wall of the feeding tube and presents a support surface for contact with the inner surface of the stomach probe lumen. The at least one projection may be formed as an elongate rib, as described previously, or as a bump or nodule having a curved or rounded profile, such that the support surface for contact with the stomach probe lumen is small. In this aspect of the invention, the support means again preferably comprises a plurality of projections which are distributed over the circumferential and/or longitudinal extent of the tube. By forming the projections as elongate ribs projecting outwardly from the enteral feeding tube, the tube (which is typically very thin) is rendered somewhat stiffer, which assists in preventing undesirable kinking of the tube during insertion through the stomach probe and during deployment in the patient.

According to yet another aspect, the invention provides a catheter, preferably of the type for providing fluid communication with the small intestine of a patient for nutriment supply during enteral feeding. Thus, the catheter comprises a tube which is preferably suitable for insertion into the small intestine of a patient, the tube defining a lumen for conveying liquid nutriment from an inlet at a proximal end of the tube to one or more outlet openings formed at a distal end region of the tube. Furthermore, a substantial proportion of the outer surface of the tube is adapted to reflect visible light having a wavelength less than or equal to 550 nm and substantially not reflect visible light having a wavelength greater than 550 nm.

In this regard, a substantial proportion of the outer surface of the tube may be generally considered to be at least 30% of the outer surface area. Preferably, the substantial proportion of the outer surface of the tube is greater than 40% of the outer surface area, more preferably greater than 60% of the outer surface area, and most preferably greater than 80% of the outer surface area of the tube. Indeed, the whole outer extent of the tube may be provided with the above optical properties.

In a preferred form of the invention, the outer surface of the tube is adapted to reflect visible light having a wavelength in the range of about 420 nm to 520 nm, more preferably in the range of 440 nm to 500 nm, and to absorb visible light having a wavelength greater than 500 nm.

Surprisingly, it has been found that catheters, such as those used for enteral feeding, are significantly more visible under observation using endoscope illumination when they are provided with the above-described optical properties. In particular, a color treatment of the tube in the blue range, and to some extent also in the green range, of the visible light spectrum renders the catheter significantly easier to identify and locate during an endoscopic procedure. This means that the medical professional responsible can more readily determine the current position and orientation of the probe, thereby simplifying the insertion procedure.

In a preferred form of the invention, the optical properties of the outer surface of the tube are provided by a suitable pigment or dye in the tube material.

Thus, expressed in another way, the invention provides a catheter for providing fluid communication with the small intestine of a patient for nutriment supply during enteral feeding, wherein the catheter comprises a tube to be inserted into the small intestine of a patient, the tube defining a lumen for conveying liquid nutriment from an inlet at a proximal end of the tube to one or more outlet openings formed at a distal end region of the tube, and wherein the tube material comprises a pigment or dye providing a substantial proportion of the outer surface of the tube with a color in the violet range or in the blue range or in the green range.

The tube may have a single layer structure or a multi-layered structure, and be formed, for example, by co-extrusion. In the case of a multi-layered structure, the desired optical properties may be provided in the material of the outer layer, but more preferably in both the outer layer and an adjacent inner layer. The outer layer of the feeding tube preferably has a Shore hardness in the range of about 40 D to 70 D, and more preferably in the range of about 50 D to about 60 D. The outer layer is preferably relatively thin, with the adjacent layer being substantially softer and thicker.

When the outer layer of the feeding tube is relatively thin, it is preferable that both the outer layer and the inner layer include a suitable pigment or dye in the tube material. In this respect, the outer layer and the inner layer of the tube may have different color tones such that, when combined, the outer surface of the tube has the desired optical properties. The provision of different color tones in the outer layer and the inner layer of the tube makes the boundary between the two layers more easily recognizable. This, in turn, has the advantage that the quality control and testing of the tube in the production process, e.g. via an optical examination during a wall-thickness measurement, may simplified and improved. In this connection, the color tone of inner layer may be made lighter or darker than the color tone of the outer layer of the tube.

Accordingly, in a further aspect, the invention provides a catheter for providing fluid communication with the small intestine of a patient for nutriment supply during enteral feeding, wherein the catheter comprises a multi-layer tube to be inserted into the small intestine of a patient, the tube defining a lumen for conveying liquid nutriment from an inlet at a proximal end of the tube to one or more outlet openings formed at a distal end region of the tube. An outer layer of the tube comprises a pigment or dye providing the outer layer with a first color tone and an adjacent inner layer comprises a pigment or dye providing the inner layer with a second color tone different from the first color tone. The second color tone is preferably in the same basic color range as the first color tone, and may have a darker or lighter shade than the first color tone.

The tube itself is preferably formed from a thermoplastic polymer material selected from the group consisting of: polyurethane, polyamide, polypropylene, and any copolymer or block copolymer comprising one or more thereof. The outer surface of the tube may also be 'frosted' by micro-roughening.

As already noted, the tube of the enteral feeding catheter is adapted to be inserted into the small intestine through a stomach probe. To this end, the tube preferably has an outer diameter of less than 5.0 mm, more preferably less than 4.0 mm, and most preferably less than or equal to 3.5 mm. The lumen of the tube typically has a diameter in the range of about 1.0 mm to 3.0 mm, and more preferably in the range of about 1.5 mm to 2.5 mm.

According to still a further aspect, the invention provides a catheter system comprising: a stomach probe for gastric decompression or drainage of stomach fluids, comprising a tube to be inserted into the stomach of a patient, the tube having proximal and distal ends and defining a lumen for receiving and for guiding insertion of a jejunal probe into the small intestine of the patient; and a jejunal probe consisting of a catheter with optical properties as described above.

According to another aspect, the invention provides a catheter for providing fluid communication with the small intestine of a patient for nutriment supply during enteral feeding, comprising a tube to be inserted into the small intestine of a patient, the tube defining a lumen for conveying liquid nutriment from an inlet at a proximal end of the tube to one or more outlet openings formed at a distal end region of the tube, wherein the distal end region of the tube comprises means for enhancing engagement between the small intestine and the tube.

In one preferred form of the invention, the engagement enhancing means comprises a section of material adapted to absorb intestinal fluid. The material section is applied at an outer surface of the distal end region of the tube and preferably has an open-pore structure which enables the section of material to take up fluid from the intestine. In particular, the material is preferably a foamed polymer material having a three-dimensional structure of interconnecting pores. In this regard, the internal surface of the three-dimensional pore structure for such a foamed polymer material is significantly larger than the external surface. The material may have a porosity of, for example, 75 percent. Open-pore silicone foams are highly preferred, as silicone materials are extremely stable in the body and do not suffer from degradation due to bodily enzymes, as is the case for some polyurethane foams. Furthermore, silicone foams are soft and thereby avoid trauma to the sensitive tissues of the intestine.

When the distal end region of the catheter tube is introduced into the small intestine for nutriment supply, the section of material having the open-pore structure absorbs fluid from the intestine under the action of osmotic and capillary forces. That section of material thus becomes heavier and expands. The increased weight of the material section then serves to anchor the end region of the catheter tube in the intestine and the enlargement or expansion of the material section provides a frictional interaction with the intestinal wall.

The section of material is preferably in the form of a sleeve or layer provided at the outer surface of the catheter tube. To position and secure the sleeve section on the distal end region of the tube, the sleeve of foam material may be coated with or immersed in an appropriate (preferably volatile) liquid. For silicone foams, for example, n-heptane may be suitable. The sleeve section takes up the liquid, causing the sleeve to expand so that it may be readily applied over the distal end of the catheter tube. The liquid is then vaporized or evaporated from the sleeve section, which shrinks the sleeve onto the outer surface of the tube. The shrinking of the sleeve onto the tube preferably also bonds the sleeve to the tube, although the bonding process may be facilitated with additional adhesive or bonding compounds.

In one form, therefore, the engagement enhancing means comprises an elongate sleeve of a foamed polymer material in the distal end region of the tube. As a variation, however, the engagement enhancing means may comprise a plurality of short sleeve sections of the foamed polymer material spaced apart at intervals in the distal end region of the tube. Each of the short sleeve sections may then form a node-like enlargement along the tube when the catheter is deployed in the small intestine. That is, each sleeve section forms a localised enlargement through the absorption of intestinal fluid. The enlargements are relatively heavy and thereby act to anchor the distal end of the tube in position. Furthermore, the localised enlargements provide a frictional engagement with the irregular surface of the intestine wall.

In a preferred form of the invention, therefore, the means for enhancing engagement between the small intestine and the tube comprises at least one node formation in the distal end region of the tube, and preferably a plurality of node formations which are spaced apart at intervals along the length of the distal end region. Each node formation typically includes an enlargement or protuberance having a diameter greater than an outer diameter of the tube. Thus, the node formation(s) is/are arranged at the distal end region of the tube for interaction with the wall of the small intestine.

In one particular form of the invention, each node formation may comprises an irregular or non-uniform surface profile. For example, each node formation may include one or more indentation and/or protuberance for interaction and engagement with the irregular surface of the wall of the small intestine. In this connection, each node formation may be constituted by a deformation of the tube.

Furthermore, the engagement enhancing means preferably includes the formation of the tube with a coiled or helical shape in the distal end region such that, in use, the distal end region of the tube is biased to engage with the wall of the small intestine.

According to a further aspect, the invention provides a method of manufacturing a catheter having the engagement enhancing means described above, the method comprising the steps of:

providing a tube formed from a thermoplastic polymer material;

providing one or more sleeve section formed from a foamed polymer material;

expanding the sleeve section;

placing the expanded sleeve section around a distal end region of the tube;

shrinking the expanded sleeve section onto the tube; and bonding the sleeve section to the tube.

In a preferred form of the invention, the step of expanding the sleeve section comprises applying a liquid to the sleeve section which causes the sleeve section to expand. Furthermore, in this preferred form of the invention, the step of shrinking the expanded sleeve section onto the tube comprises evaporating the liquid from the expanded sleeve section to shrink the sleeve section onto the tube. Preferably, the step of shrinking the expanded sleeve section onto the tube also bonds the sleeve section to the tube.

According to yet a further aspect, the invention provides a method of manufacturing a catheter having the node formations described above, the method comprising the steps of:

providing a tube formed from a thermoplastic polymer material;

heating the tube at one or more localized positions to soften the thermoplastic polymer material at each localized position;

pressurizing the inside of the tube to deform the softened thermoplastic polymer material; and moulding the softened thermoplastic polymer material to a desired node formation during the pressurizing step.

In a preferred form of the invention, the step of pressurizing the inside of the tube comprises connecting the tube to a source of pressurized gas, such as pressurized air, pressurized carbon-dioxide or pressurized nitrogen.

In a preferred form of the invention, the step of moulding the softened thermoplastic polymer material involves deforming the material under pressurization into a mould arranged, e.g. clamped, around the tube at each localized position.

Thus, in a still further aspect, the invention provides a catheter system including: a stomach probe for gastric decompression or drainage of stomach fluids, comprising a tube to be inserted into the stomach of a patient, the tube having proximal and distal open and defining a lumen for receiving and for guiding insertion of a jejunal probe into the small intestine of the patient; and a jejunal probe consisting of a catheter having means for enhancing engagement between the small intestine and the tube as described above.

The present invention will now be described by way of example with reference to particular embodiments illustrated in the accompanying drawings. It should be understood, however, that the following description of preferred embodiments is not intended to limit the generality of the inventive concept as described above or as defined in the appended claims.

BRIEF DESCRIPTION OF THE DRAWINGS

Preferred embodiments of the invention are hereafter described with reference to the accompanying drawing figures, in which like reference characters designate like features, and in which:

FIG. 2 is a side view of the stomach probe shown in FIG. 1;

FIG. 3 is a schematic sectioned side view of the distal end region of the stomach probe shown in FIG. 2;

FIG. 4 is a cross-section at "X-X" of the stomach probe shown in FIG. 2 according to one embodiment of the invention;

FIG. 5 shows the detail "A" from FIG. 4;

FIG. 6 shows a cross-section from "X-X" of the stomach probe in FIG. 2 according to another embodiment of the invention, and including a partial schematic illustration of the twisted or helical nature of the rib-like projections;

FIG. 7 is a cross-section at "X-X" of the stomach probe shown in FIG. 2 according to a further embodiment of the invention;

FIG. 8 shows the detail "B" from FIG. 7;

FIG. 9 is a cross-section at "X-X" of the stomach probe shown in FIG. 2 according to yet another embodiment of the invention;

FIG. 11 is a side view of the jejunal probe shown in FIG. 1;

FIG. 12 illustrates the jejunal probe of FIG. 11 in a straightened configuration;

FIG. 13 is a side view of the distal end region of the jejunal probe shown in FIG. 12;

FIG. 14 illustrates the coiled configuration of the distal end region of the jejunal probe shown in FIG. 11;

FIG. 15 is a cross-section at "Y-Y" of the jejunal probe shown in FIG. 11;

DETAILED DESCRIPTION OF THE PREFERRED EMBODIMENTS

Figure 1:
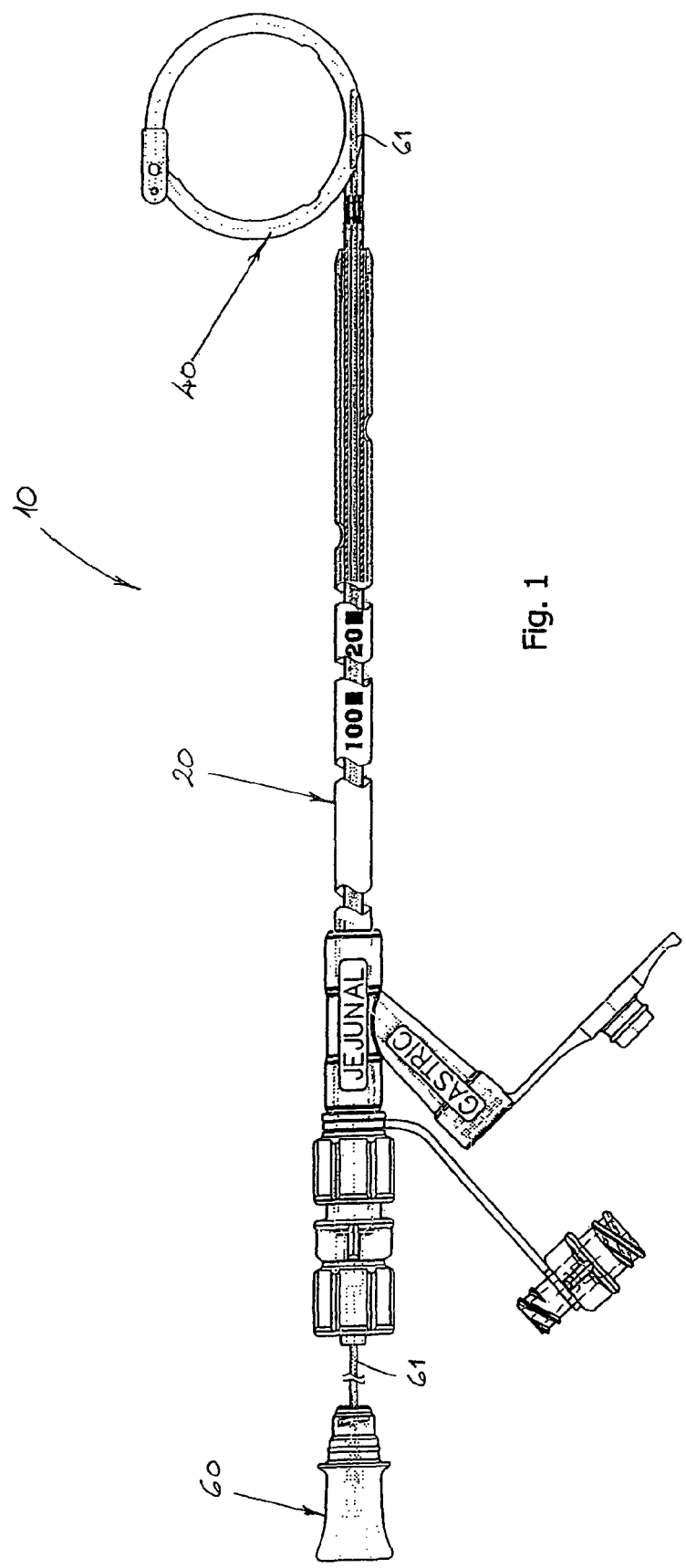
FIG. 1 is a side view of a catheter system according to the invention comprising a stomach probe and a jejunal probe in combination.

Referring firstly to FIG. 1 of the drawings, an example of an assembled catheter system 10 according to the invention is illustrated. The catheter system 10 comprises a stomach probe 20 for providing fluid communication with the stomach of a patient for gastric decompression or drainage of stomach fluids, and a jejunal probe 40 received within and extending through the stomach probe 20 for providing fluid communication with the small intestine of a patient for nutriment supply during enteral feeding. The catheter system 10 also includes a guide wire device 60 having an elongate guidewire 61 which is inserted into the jejunal probe 40 to provide some rigidity for assisting insertion of the jejunal probe 40 through the stomach probe 20 and into the small intestine of the patient. The various components of the catheter system 10 will now be described in more detail with reference to the other drawings.

FIG. 2 of the drawings illustrates the general construction of the stomach probe 20. In this regard, the stomach probe 20 is a catheter comprising a tube 21 having a proximal end 22 and a distal end 23. The tube 21 is open at each of its proximal and distal ends 22, 23 and defines a single lumen 24 extending centrally along the entire length thereof between the proximal and distal ends. The lumen 24 has two primary functions. Firstly, it is designed to provide fluid communication with the stomach of a patient for performing gastric decompression and/or drainage of stomach fluids. Secondly, it is designed to receive the jejunal probe 40 for guiding the insertion of the jejunal probe to the small intestine of the patient.

The proximal end 22 of the stomach probe 20 is secured, e.g. by adhesive bonding, to a connector element 25 having a generally Y-shaped configuration. This Y-shaped connector has two ports 26, 27 providing fluid communication with the lumen 24 of the tube 21. The first port 26, which is generally aligned with a longitudinal axis of the tube 21, is designed for the insertion of the jejunal probe there-through. Hence, this portion of the Y-connector 25 is labeled "JEJUNAL". This probe-insertion port 26 of the Y-connector 25 is also provided with a threaded closure element 28 for sealing the probe-insertion port 26 when not in use.

The other laterally arranged port 27 is designed for connection to a suction source for decompressing the patient's stomach and/or draining fluids from the stomach, as needed. This suction port 27, labeled "GASTRIC", is provided with a press-sealable closure element 29 for sealing the port when it is not in use. When suction is applied at the port 27, fluids are drawn into the lumen 24 not only via an axial opening 30 at the distal end 23 of the tube, but also via a collection of lateral openings 31 formed through the tube wall 32 in a distal end region of the tube 21. As can be clearly seen in the enlarged illustration of the distal end region of the tube 21 shown in FIG. 3, these lateral openings 31 are spaced apart from one another and offset on opposite sides of the tube 21. The spacing S between adjacent lateral openings 31 on the same side of the tube is typically in the range of about 30 mm to about 40 mm and the overall length of the distal end region of the tube 21 provided with these lateral openings 31 is about 200 mm. The overall length L of the tube 21 itself is about 1100 mm.

Details of the internal structure of the tube 21 according to alternative embodiments of the stomach probe 20 are illustrated in FIGS. 4 to 9.

Referring firstly to FIG. 4 of the drawings, one particular example of a cross-section of the tube 21 at X-X in FIG. 2 is illustrated. The tube 21 is typically formed by extrusion from a thermoplastic polyurethane material having a hardness in the range of about Shore 50 A to 80 A, and having an outer diameter $D_o$ in a range of about 5 to 6 mm and an inner diameter $D_i$ in a range of about 3.5 to 4.5 mm. The relatively soft polyurethane material is desirable for preventing trauma or injury to the sensitive mucous membranes of the nose, throat, oesophagus and stomach during insertion and use, while the outer diameter $D_o$ is effectively limited by the size of the nasal cavities through which the stomach probe 20 is typically inserted.

An important characteristic of the cross-section of the tube 21 in the stomach probe of the invention is the presence of several triangularly cross-sectioned projections 34 which project inwardly from the wall 32 of the tube into the lumen 24. In the particular example of the tube illustrated in FIG. 4, the stomach probe 20 has twenty individual projections evenly distributed in the circumferential direction and angularly spaced from one another at intervals of about 18°. Furthermore, it will be appreciated that each of the projections 34 illustrated in FIG. 4 extends longitudinally of the tube such that each of the projections 34 is actually formed as an elongate rib, typically following a curved or helical path.

A more detailed view of the cross-section of each of these rib-like projections 34 is illustrated in FIG. 5. In particular, it can be clearly seen that each of the ribs has an essentially triangular cross-section which tapers uniformly at an angle of about 70° in the radially inward direction from a broad base region adjacent the wall 32 of the tube to a relatively small rounded tip area 35 which extends as a ridge along the length of the rib. Each tip or ridge 35 of the ribs 34 forms a support against which the outer surface of the jejunal probe 40 may come into contact during insertion of the jejunal probe through the lumen 24 of the stomach probe 20. Because the tip or ridge 35 of each rib-like projection 34 has such a small rounded surface area, the projections effectively make only line contact with the outer surface of the jejunal probe. Accordingly, this results in very low contact area and low surface friction between the jejunal probe 40 and the stomach probe 20.

Each of the rib-like projections 34 has a height h in the range of about 0.05 mm to 0.5 mm, and more preferably of about 0.2 mm. This gives rise to the dimension $D_p$ which represents the diameter between opposite projections 34. Thus, another advantage of the projections 34 is that they ensure the jejunal probe 40, when inserted through the lumen 24 of the stomach probe 20, always maintains at least a minimum spacing—equivalent to the height h—from the inner surface of the wall 32 of the tube. In this way, even when the outer surface of the jejunal probe is in contact with the tip or ridge areas 35 of the projections, a circumferential gap or spacing between the inner surface of the tube wall 32 and the outer surface of the jejunal probe 40 is maintained. This prevents the lateral holes 31 in the distal end region of the tube 21 from being blocked or even partially blocked by the jejunal probe 40. In this way, the rib-like projections 34 are effectively adapted to form channels (i.e. between each pair of adjacent rib projections) for conveying or guiding the flow of stomach fluids evacuated through the tube 21 to the suction port 27.

The twenty helical rib-like projections 34 in the embodiment of FIG. 4 are formed with a pitch of approximately one circumferential traverse of the lumen 24 for each 1.0 meter length of the tube 21. While this provides a highly desirable configuration, it will also be appreciated that the pitch of these twenty helical ribs may range between one circumferential traverse of the lumen per 0.3 meter length of the tube, and one circumferential traverse of the lumen per 3.0 meter length of the tube 21.

FIG. 6 of the drawings illustrates another embodiment similar to that shown in FIG. 4, with the only major difference being a reduced number of the projections 34. Specifically, in the embodiment of FIG. 6, only ten elongate rib-like projections are formed along the length of the tube 21, with the ribs again being evenly distributed around the circumferential extent of the tube—this time angularly offset at intervals of about 36° from one another. In this case, the pitch of the helically extending ribs 34 is typically one circumferential traverse of the lumen per 0.5 meter length of the tube 21. FIG. 6 provides a schematic illustration (in broken lines) of the course of the helical ribs around the tube 21. In this regard, each of the broken lines effectively represents the ridge of each of the tapered rib projections 34. The actual shape of the rib projections 34 remains essentially unchanged from that shown in FIG. 5.

The present invention also contemplates an embodiment of the stomach probe 20 having just a single twisted or helical rib projection 34. In such a case, the rib would desirably have a pitch in the range of one circumferential traverse of the lumen 24 per 5 mm to 20 mm length of the tube 21. At the other extreme, the invention also contemplates an embodiment of the stomach probe 20 having as many as forty rib-like projections 34, where the pitch of each helical rib is again within the range of one circumferential traverse of the lumen per 0.3 to 3.0 meter length of the tube 21, this time preferably one circumferential traverse per 2.0 meters length of the tube.

Each of the tubes 21 illustrated in the embodiments of FIG. 4 and FIG. 6 are manufactured in an extrusion process through an extrusion die (not shown), which has a cavity defining the circular shape of the tube wall 32 and evenly spaced triangular recesses corresponding to the shape of the projections 34. The triangular recesses in the extrusion die are in communication with the angular wall cavity such that material extruded through the wall-forming cavity of the die may also be extruded through the triangular recesses to thereby produce the tube wall 32 and the projections 34 as an integral formation. The projection-forming triangular recesses of the extrusion die are naturally oriented radially inwardly in correspondence with the desired orientation of the projections.

During the extrusion process, the extrusion die—which is typically provided in an extrusion nozzle—may be rotated such that the elongate rib-like projections 34 formed by the extrusion of material through the triangular recesses, are generated with a twist. In this way, the rib-like projections 34 may then extend in a helical form both longitudinally and circumferentially along the wall 32 of the tube 21. The angle or pitch of the helical ribs 34 can be adjusted depending upon the rate of rotation of the extrusion nozzle, as well as the rate of feed of the thermoplastic material through the die. Thus, the ribs 34 may define helical channels there-between for conveying or guiding the flow of stomach fluids evacuated through the tube. Furthermore, the helical form of the rib-like projections 34 may be adapted to assist forward advancement of the jejunal probe 40 through the tube as the jejunal probe is being inserted or deployed (e.g. when the probe 40 is rotated).

During the extrusion process for manufacturing the tube 21, at least one strip 36 of treated and/or colored material is co-extruded into the tube wall 32. Each elongate strip 36 is a so-called X-ray strip and includes a radiopaque substance, such as barium sulfate, for enhancing observation and identification of the stomach probe within the patient during a radiographic (i.e. X-ray) investigation. Each strip 36 may also be colored to contrast with the rest of the tube material for visual identification during an endoscopic investigation. The tube 21 preferably has three of the strips 36 equally spaced around its periphery and extending longitudinally thereof for optimal X-ray recognition, but it may have as few as just one strip or as many as five.

With reference now to FIGS. 7 to 9 of the drawings, two further embodiments of the stomach probe 20 are illustrated. The embodiment in FIG. 7 corresponds in the number, shape and arrangement of the projections 34 to the embodiment described with reference to FIG. 4. The main difference in the embodiment of FIG. 7 is that the wall 32 of the tube 21 consists of two co-extruded layers comprising an outer layer 37 and an inner layer 38. The material of the outer layer 37 is again preferably a relatively soft thermoplastic polyurethane corresponding to the material in the embodiment of FIG. 4. The reason for this relatively soft material in the outer layer is again to minimize trauma to the sensitive mucous membranes and tissues with which the tube 21 comes into contact.

The inner layer 38 of the tube is substantially thinner than the outer layer 37 and includes the projections 34 as integral formations. The thickness 't' of the inner layer is typically in the range of about 0.05 to 0.2 mm, compared with a thickness in the range of about 0.5 to 0.9 mm in the outer layer. The inner layer 38 is formed from a somewhat harder thermoplastic polymer than the outer layer 37, and typically has a hardness in the range of Shore 40 D to 70 D, and more preferably 50 D to 60 D. The inner layer 38 may again be formed from a polyurethane, or alternatively from any other suitable thermoplastic polymer material, such as polyamide. This harder inner layer 38, which also includes the projections 34, contributes to a reduction in the surface friction between the projections 34 and the outer surface of the jejunal probe inserted through the lumen of the stomach probe 20. The same applies for the embodiment shown in FIG. 9, with the only difference being the reduced number of rib projections 34; namely ten helically extending elongate ribs angularly distributed at intervals of about 36° around the circumference of the wall 32 of the tube—as was the case for the embodiment in FIG. 6. The material combination of a softer polyurethane (PUR) for the outer layer 37 and a harder polyamide (PA) for the inner layer 38 has been found to be particularly advantageous with regard to the resultant low friction properties.

Figure 10A:
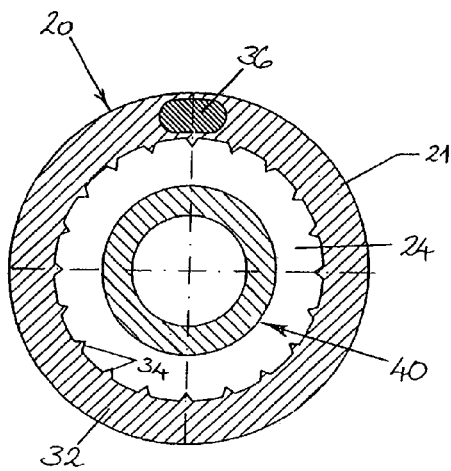
FIGS. 10A to 10D are cross-sections of the stomach probe embodiments in FIGS. 4, 6, 7 and 9, respectively, in combination with a jejunal probe.
Figure 10B:
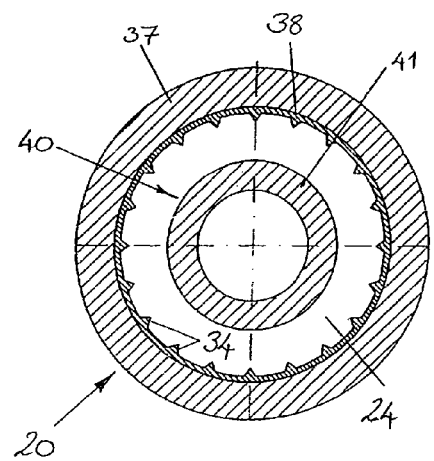
Figure 10C:
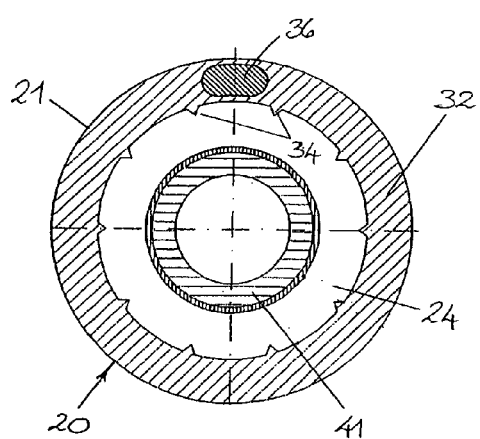
Figure 10D:
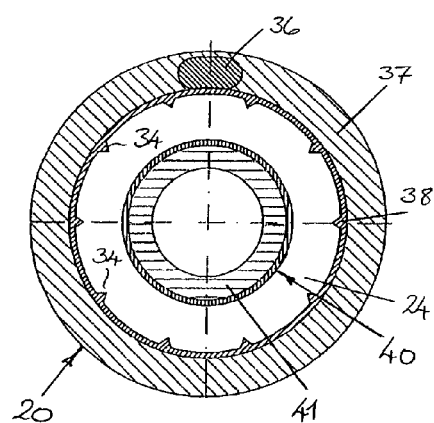

FIGS. 10A to 10D illustrate the various embodiments of the stomach probe described with reference to FIGS. 4 to 9 in combination with a tube 41 of a jejunal probe 40 arranged centered within the lumen 24 of the stomach probe tube 21. In each case, the dimensions of the stomach probe 20 and of the jejunal probe 40 are selected to provide a sufficient annular spacing between the two probes to enable optimal decompression or drainage of the stomach through the annular space or gap between the wall 32 of the stomach probe tube 21 and the outer surface of the jejunal probe tube 41. The sizing of the stomach probe tube 21 and the jejunal probe tube 41 in FIGS. 10A to 10D is merely schematic for illustrative purposes, and shows the jejunal probe tube 41 positioned centered within stomach probe. It will be appreciated, however, that in use the tube 41 may be displaced to an eccentric position within the stomach probe and contact the projections 34. Furthermore, the outer diameter of the jejunal probe tube 41 may be larger than that shown so that the outer surface of the tube 41 is generally closer to the projections 34. As noted above, however, the projections 34 ensure the maintenance of a minimum circumferential spacing between the two probes 20, 40 for effective decompression and/or drainage of the stomach, i.e. through the channels formed between each of the adjacent projections 34. As shown in FIGS. 10A and 10B, the tube 41 of the jejunal probe 40 may have a single-layered construction or, alternatively, as shown in FIGS. 10C and 10D, may have a multi-layered structure presenting a relatively thin outer layer of a harder material and a thicker inner layer of a softer material.

Details of the jejunal probe 40 will now be more fully described with reference to drawing FIGS. 11 to 15. The jejunal probe 40 is a catheter for providing fluid communication with the small intestine of a patient for nutriment supply during enteral feeding. It comprises a tube 41 which has a proximal end 42 and a distal end 43 and defines a lumen 44 for conveying liquid nutriment from an inlet at the proximal end 42 to a plurality of outlet openings 45 formed in a distal end region of the feeding tube. The inlet to the lumen 44 is provided by a connector element 46, which is secured (e.g. by adhesive bonding) to the proximal end 42 of the tube 41.

The connector 46 is designed for threaded coupling in the first port 26 of the Y-connector 25 of the stomach probe to secure the jejunal probe 40 within the catheter system 10 after it has been deployed in the intestine of the patient.

As can be more clearly seen in FIGS. 12 and 13, the outlet openings 45 comprise four oval-shaped openings having a length $I_o$ of about 3 mm and which are formed spaced apart at intervals s of about 25 mm in opposite side walls of the tube 41. At the distal end 43, the feeding tube is provided with a tip member 46 which is typically secured to the tube by adhesive bonding. The tip member 47 has a closed rounded end but includes small side openings to prevent any accumulation or stagnation of the liquid nutriment at the tip end of the jejunal probe. This closed tip member 47 serves as a stop for an end 62 of the guidewire or stylet 61 which is inserted into the feeding tube 41 to enhance rigidity while the tube is being slid through the stomach probe 20 to the enteral deployment site.

As is apparent from FIG. 11 and FIG. 14, the distal end portion of the tube 41 is formed in a circular coil having a diameter of about 30 mm. As is evident from FIG. 1 and FIG. 11, the coiled portion of the jejunal probe 40 is the distal end portion which incorporates the lateral outlet openings 45. Accordingly, the coiled portion of the tube 41 is that portion which, when deployed, extends within the small intestine of the patient to the enetral feeding site. Thus, this coiled region typically has an overall length $I_d$ in the range of about 200 to 300 mm.

Because this distal end region of the feeding tube 41 is formed coiled, it naturally needs to be straightened before it can be inserted through the lumen 24 of the stomach probe 20. To this end, the guide wire device 60 is employed. The guide wire, which is relatively less flexible than the jejunal probe 40, is inserted into the feeding tube 41 in order to straighten the tube before it is inserted through the stomach probe 20 and guided towards the small intestine. Once the feeding probe 20 is inserted into the small intestine, the guide wire device 60 is withdrawn. Removal of the guidewire 61 causes the distal end region of the feeding tube 41 to tend to return to its coiled shape, which in turn biases that part of the tube into engagement with the wall of the intestine. This assists in holding the tube in its deployed position.

The cross-sectional construction of the feeding tube 41 is illustrated in FIG. 15. The outer diameter $d_o$ of the tube 41 is typically in the range of about 2.0 to 4.0 mm and the inner diameter $d_i$ of the tube 41 (i.e. the diameter of the lumen 44) is typically in the range of about 1.0 to 3.0 mm. As can be seen, the two co-extruded layers of the tube previously noted in FIGS. 10C and 10D of the drawings are illustrated. The outer layer 48 is relative thin with a thickness $t_1$ in the range of about 0.02 mm to 0.2 mm and is formed from a thermoplastic polymer material having a higher hardness, e.g. in the range of about Shore 40 D to 70 D, than the material of the inner layer 49. The overall wall thickness T, by contrast, is in the range of about 0.4 to 0.6 mm. The inner layer 49 is formed of a relatively soft thermoplastic polymer material, such as polyurethane, having a Shore hardness in the range of 50 A to 80 A (as for the outer layer of the stomach probe tube 21). Although the outer layer 48 may be formed from polyurethane, other materials such as polyamide are also contemplated. The advantage of this thin outer layer 48 formed from a harder polymer material is again a reduction in friction between the outer surface of the feeding tube 41 and the protrusions 34 during insertion of the jejunal probe 40. In this connection, it will be noted that the protrusions 34 may also be formed on a harder inner layer 38 of a co-extruded stomach probe tube 21. The thin outer layer 48 provides the benefit of a reduced friction coefficient without rendering the tube 41 too hard or too stiff overall.

The polymer material of the feeding tube 41 is typically formed to be radiopaque, e.g. by the addition of a radiographically detectable substance, such as barium sulfate, in order that the position of the probe can be determined radiographically (i.e. by X-ray). Furthermore, to significantly enhance the visibility of the feeding tube when illuminated by an endoscope, both the outer layer and the inner layer of the feeding tube is provided with pigmentation or dye which causes substantially the entire extent of the tube to reflect visible light having a wavelength in the range of 440 nm to 500 nm, i.e. in the blue range, and to absorb visible light having a wavelength greater than 500 nm. The tube 41 thereby has the significant advantage that it can be much more readily detected in a video image generated using standard endoscope equipment. Catheters of this type for enteral feeding have conventionally been fabricated from transparent polymer materials and have, as a result, been extremely difficult to locate visually using an endoscope. Although catheters having various optical properties have been tested, jejunal probes designed to reflect visible light in this blue range surprisingly have been found to provide the most significantly improved visibility compared to the others. It will be noted that catheter tubes having coloring in the indigo range from 420 nm to 440 nm can also provide good results, as can catheter tubes with coloring into the green range, e.g. up to 520 nm.

Figure 16:
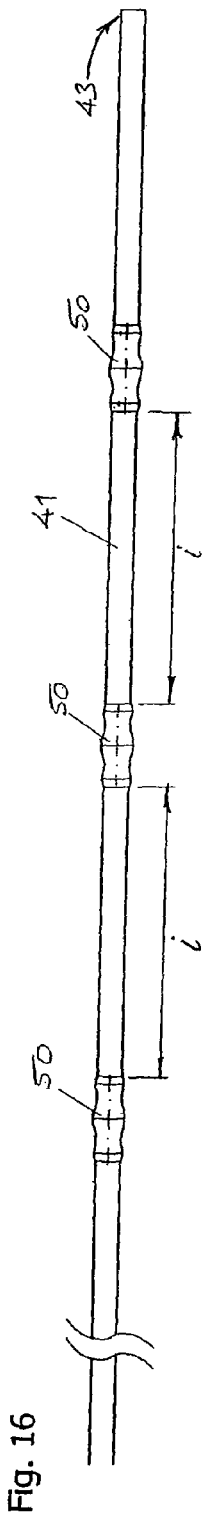
FIG. 16 is a side view of a distal end region of the tube of a jejunal probe according to an embodiment of the invention.
Figure 17:
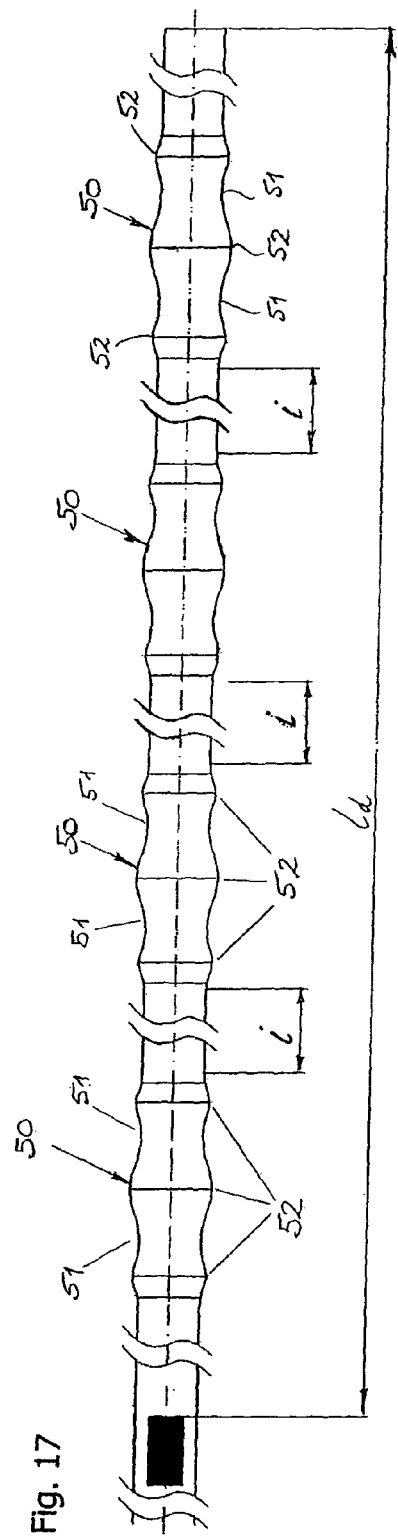
FIG. 17 illustrates in more detail the distal end of the jejunal probe shown in FIG. 16.

FIGS. 16 and 17 of the drawings illustrate a further modification of the jejunal probe according to the invention. These drawings show the distal end region of the feeding tube 41 without the tip member 47 and, in this embodiment, the tube 41 comprises a number of node formations 50 spaced apart from one another at intervals i in the range of about 30 mm to 40 mm in the distal end region of the tube. The length $I_d$ of the distal end region of the tube 41 incorporating the node formations 50 generally corresponds to the length of the coiled portion of the tube, namely between about 200 mm and 300 mm.

Each of the node formations 50 has an irregular or non-uniform surface profile, which may be generally described as 'wavy', and includes two indented regions 51 and three enlarged or protruding regions 52. These enlarged or protruding regions 52 having an outer diameter somewhat greater than the standard outer diameter $d_o$ of the rest of the feeding tube 41. Indeed, the outer diameter of these enlarged regions in typically in the range of 1.0 to 2.0 times the outer diameter $d_o$ of the feeding tube 41, and more preferably in the range of 1.0 to 1.5 times the outer diameter $d_o$ of the feeding tube 41. Similarly, the indented regions may have an outer diameter in the range of 1.5 to 0.8 times the outer diameter $d_o$ of the feeding tube. Note the outer diameter of the indented region 51 can be larger than the outer diameter $d_o$ of the tube 41 if the diameter of the enlarged region 52 is even greater.

Thus, the irregular profile of each node formation 50 provides surfaces or geometries which are able to interact with and engage with the wall of the small intestine. That is, the presence of these node formations 50 in the coiled portion of the tube 41 serves to substantially enhance the engagement between the tube and the wall of the small intestine as the tube curls into contact the intestinal walls upon removal of the guidewire 61.

In this regard, it will be appreciated that the walls of the small intestine are not smooth, but rather have a corrugated or irregular surface created by numerous finger-like projections (i.e. villi) from the mucous membrane of the intestinal wall. Thus, after the guidewire 61 is removed and the distal end region of the tube 41 tends to return to its original coiled shape, the node formations 50 come into contact with the walls of the small intestine. The non-uniform, wavy-shaped node formations 50 formed in the wall of the jejunal feeding tube 41 thereby interact with and find purchase with the irregular surface of the intestine which helps hold the distal end region of the feeding probe 40 in its desired deployed position.

Each of the node formations 50 may be produced by deforming the thermoplastic polymer material of the tube 41 itself. In this regard, the method of manufacturing the jejunal probe according to the embodiment of FIGS. 16 and 17 typically includes the steps of:

heating the tube at localized positions to soften the thermoplastic polymer material of the tube wall at each of those positions;

arranging a mold conforming to a desired final shape of a node formation 50 at each of the localized positions where the thermoplastic polymer material of the tube is heated and softened; and connecting the tube 41 to a source of pressurized gas such that the inside of the tube is pressurized to deform the softened thermoplastic polymer material into the mold arranged at each of the localized positions where the thermoplastic material has been softened.

In this way, the material of the tube 41 is deformed into the mold to provide the desired node formations 50 at each of the localized positions selected. After this molding process is completed, the internal pressurization of the tube is removed and the molded local portions are cooled, such that the tube material at those positions becomes firm again. The desired node formations 50 are thereby set in wall of the thermoplastic tube 41.

Figure 18:
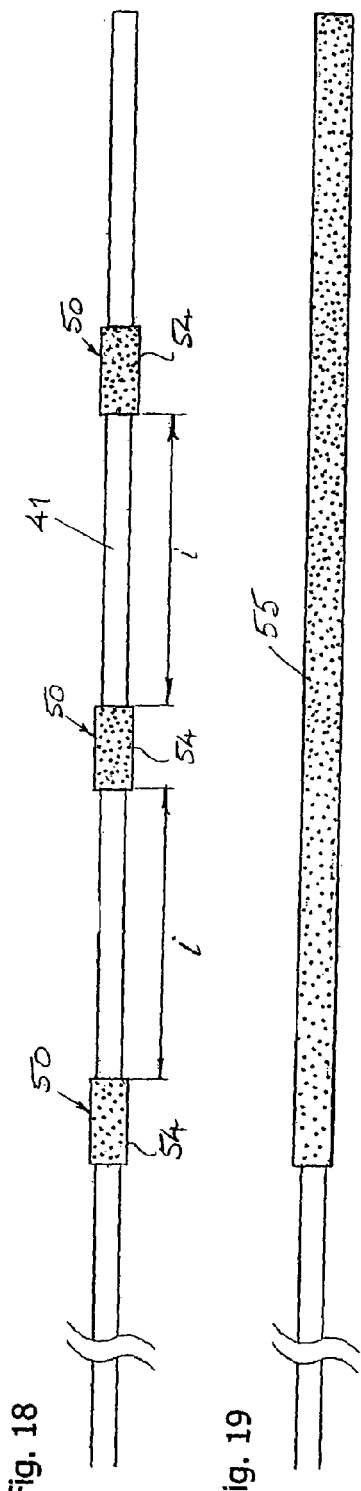
FIG. 18 is a side view of a distal end region of the tube of a jejunal probe according to another embodiment of the invention.

FIG. 18 of the drawings illustrates yet another modification of the jejunal probe according to the invention. This drawing again shows the distal end region of the feeding tube 41 without the tip member 47 and, in this embodiment, the distal end region of the tube 41 again comprises a number of node formations 50 spaced apart from one another at intervals i in the range of about 30 mm to 40 mm. In this case, however, each of the node formations 50 comprises a short cylindrical sleeve section 54 of a foamed silicone material. The short sleeve sections 54 of foamed silicone material are bonded to the outer surface of the tube 41 and have an open-pore structure which enables the sleeve sections 54 to take up fluid from the intestine. In particular, the foamed silicone material has a three-dimensional structure of interconnecting pores, which absorb fluid from the intestine under the action of osmotic and capillary forces when the distal end region 41 of the catheter tube is introduced into the small intestine for nutriment supply. Thus, once the catheter is deployed in the small intestine for enteral feeding, the sleeve sections 54 absorb fluid and thereby expand and become heavier.

As for the embodiment in FIGS. 16 and 17, therefore, the silicone foam node formations 50 enhance engagement of the probe with the walls of the intestine. In addition, however, the increased weight of the expanded sleeve sections 54 also assists to anchor the distal end of the probe in position. To position and secure the sleeve sections 54 on the distal end region of the tube, an appropriate liquid, such as n-heptane, is applied to and taken up by each sleeve section causing it to expand, e.g. by 50%, so that it may be readily fitted over the distal end of the tube. The liquid is then vaporized or evaporated from the sleeve section, which shrinks the sleeve onto the outer surface of the tube and thereby also bonds the two together.

Figure 19:
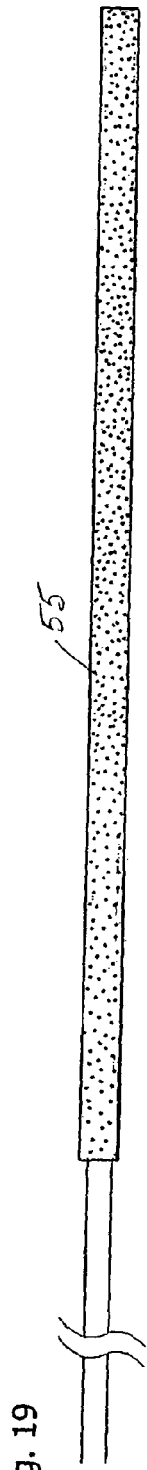
FIG. 19 is a side view of a distal end region of the tube of a jejunal probe according to a further embodiment of the invention.

FIG. 19 illustrates a variation of the embodiment shown in FIG. 18, whereby the distal end region 41 of the tube includes a single elongate outer layer or sleeve section 55 of the foamed silicone material. While this embodiment does not provide repeated variation in the outer diameter of the distal end region 41 via a series of node formations 50, the greater length of the sleeve section 55 results in an increased absorption of fluid from the intestine, producing greater weight and therefore an increased anchor effect.

It will be appreciated that, in addition to or as an alternative to any of the above described embodiments, a distally extending portion of the foamed silicone material may be attached or bonded to the distal tip member 47 of the feeding probe 40. This portion of foamed silicone material attached to the distal tip member 47 may take any appropriate form, but is it preferably elongate. When, in use, this portion of foamed silicone material absorbs intestinal fluid, it may act as a "drift anchor" extending from the distal tip member 47, thereby also assisting to hold the probe in position during the course of its deployment.

The above discussion of preferred embodiments of the invention is intended for illustrative purposes only. Accordingly, it will be appreciated that alterations may be made in the particular construction and arrangement of the parts shown in the drawings without departing from the scope of the invention as defined in the appended claims.

The invention claimed is:

1. The catheter for providing fluid communication with the small intestine of a patient for nutriment supply during enteral feeding, comprising a tube to be inserted into the small intestine of a patient, the tube defining a lumen for conveying liquid nutriment from an inlet at a proximal end of the tube to one or more outlet openings formed at a distal end region of the tube, characterized in that the distal end region of the tube comprises means for enhancing engagement with the small intestine and to assist in anchoring the distal end region of the tube in position wherein the means for enhancing engagement is made of a material that is nondigestable by body fluids.

2. The catheter according to claim 1 wherein
a substantial proportion of the outer extent of the tube is adapted to reflect visible light having a wavelength less than or equal to 550 nm and substantially not reflect visible light having a wavelength greater than 550 nm.

3. The catheter according to claim 2, wherein said substantial proportion of the outer extent of the tube is selected from the group consisting of greater than 40% of the outer surface area, greater than 60% of the outer surface area, and greater than 80% of the outer surface area of the tube.

4. A catheter according to claim 2, wherein the outer extent of the tube is adapted to absorb visible light having a wavelength greater than 500 nm and to reflect visible light having a wavelength in the range selected from the group consisting of about 420 nm to 520 nm and about 440 nm to 500 nm.

5. The catheter according to claim 2, wherein optical properties of the outer extent of the tube are provided by a pigment or dye in the tube material.

6. The catheter according to claim 5, wherein the tube has a multi-layered structure, with the outer layer of the tube having a Shore hardness in the range of 40 D to 70 D and being formed of a material including the pigment or dye.

7. The catheter according to claim 2, wherein the tube has a multi-layered structure, with the outermost layer of the tube having a Shore hardness greater than the adjacent layer.

8. The catheter according to claim 2, wherein the outer surface of the tube is frosted by micro-roughening.

9. The catheter according to claim 2, wherein the tube is adapted to be inserted into the small intestine through a stomach probe and has an outer diameter selected from the group consisting of less than 5.0 mm, less than 4.0 mm, and less than or equal to 3.5 mm.

10. The catheter according to claim 2, wherein the lumen of the tube has a diameter in the range selected from the group consisting of about 1.0 mm to 3.0 mm and about 1.5 mm to 2.5 mm.

11. The catheter according to claim 2 wherein the tube is formed of a polymer plastic material selected from the group consisting of polyurethane, polyamide, polypropylene, and any copolymer or block copolymer comprising one or more thereof.

12. The catheter according to claim 1, wherein the engagement enhancing means comprises a section of material adapted to absorb intestinal fluid.

13. The catheter according to claim 12, wherein the section of material comprises a foamed polymer material having a three-dimensional structure of interconnecting pores.

14. The catheter according to claim 12, wherein the section of material is in the form of a sleeve or layer provided at the outer surface of the catheter tube.

15. The catheter according to claim 1, wherein the engagement enhancing means comprises a plurality of sleeve sectors of a foamed polymer material spaced apart at intervals in the distal end region of the tube.

16. The catheter according to claim 1, wherein the engagement enhancing means comprises at least one node formation having a characteristic selected from the group consisting of an irregular or non-uniform surface profile comprising one or more indented regions and/or one or more enlarged or protruding regions, a deformation of the tube, and at least one enlarged or protruding region.

17. The catheter according to claim 1, wherein the engagement enhancing means includes a plurality of node formations which are spaced apart at intervals along a length of the tube.

18. The catheter according to claim 17, wherein each node formation of the plurality of node formations has an irregular or non-uniform surface profile comprising one or more indented regions and/or one or more enlarged or protruding regions.

19. The catheter according to claim 17, wherein each node formation comprises a deformation of the tube.

20. The catheter according to claim 17, wherein each node formation includes at least one enlarged or protruding region.

21. The catheter according to claim 17, wherein each node formation is arranged in a distal end region of the tube for interaction with the wall of the small intestine.

22. The catheter according to claim 16, wherein the engagement enhancing means includes formation of a distal end region of the tube in a curved or helical shape such that, in use, the distal end region of the tube is biased into engagement with a wall of the small intestine.

23. The catheter according to claim 17, wherein the engagement enhancing means includes formation of a distal end region of the tube in a curved or helical shape such that, in use, the distal end region of the tube is biased into engagement with a wall of the small intestine.

* * * * *